United States Patent [19]
Boury

[11] Patent Number: 5,916,147
[45] Date of Patent: Jun. 29, 1999

[54] SELECTIVELY MANIPULABLE CATHETER

[76] Inventor: Harb N. Boury, 120 Sunset Ave, Glen Ellyn, Ill. 60137

[21] Appl. No.: 08/934,980

[22] Filed: Sep. 22, 1997

[51] Int. Cl.[6] ........................................................ A61B 1/00
[52] U.S. Cl. ............................ 600/146; 600/139; 600/149
[58] Field of Search ..................................... 600/139, 140, 600/141, 142, 143, 144, 146, 149

[56]           References Cited

U.S. PATENT DOCUMENTS

| 4,700,693 | 10/1987 | Lia et al. . | |
| 5,174,277 | 12/1992 | Matsumaru | 600/142 |
| 5,325,845 | 7/1994 | Adair . | |

*Primary Examiner*—Beverly M. Flanagan
*Attorney, Agent, or Firm*—Niro, Scavone, Haller & Niro

[57]           ABSTRACT

A remotely steerable catheter having an elongate tubular member having a proximal end, a distal end, a remotely manipulable length, and a wall defining a lumen and first and second wires slidably retained by the wall and extending proximally beyond the proximal end of the tubular member, the first wire having a distal end thereof in controllable contact with the wall at a first node located along the manipulable length and the second wire having a distal end thereof in controllable contact with the wall at a second node located along the manipulable length, the second node being located distally of the first node along the manipulable length of the tubular member.

25 Claims, 5 Drawing Sheets

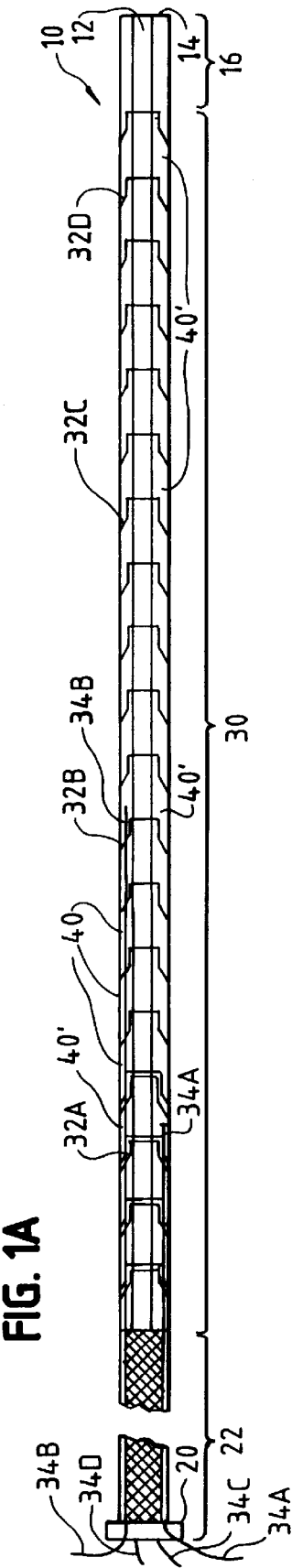
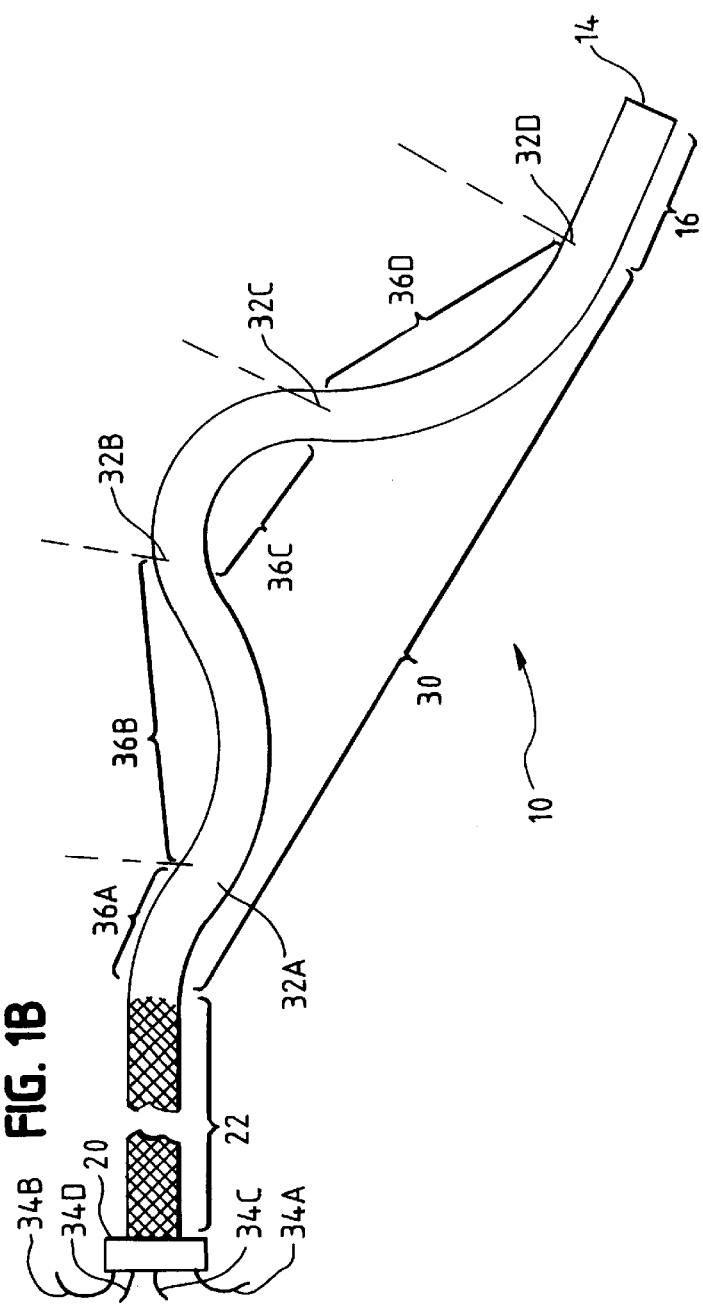

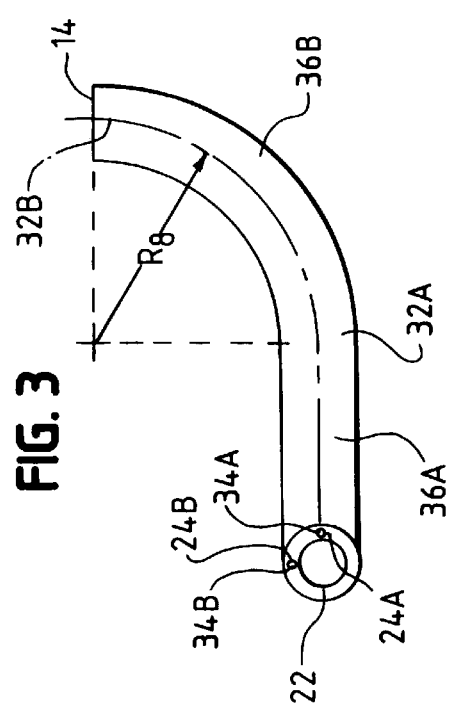
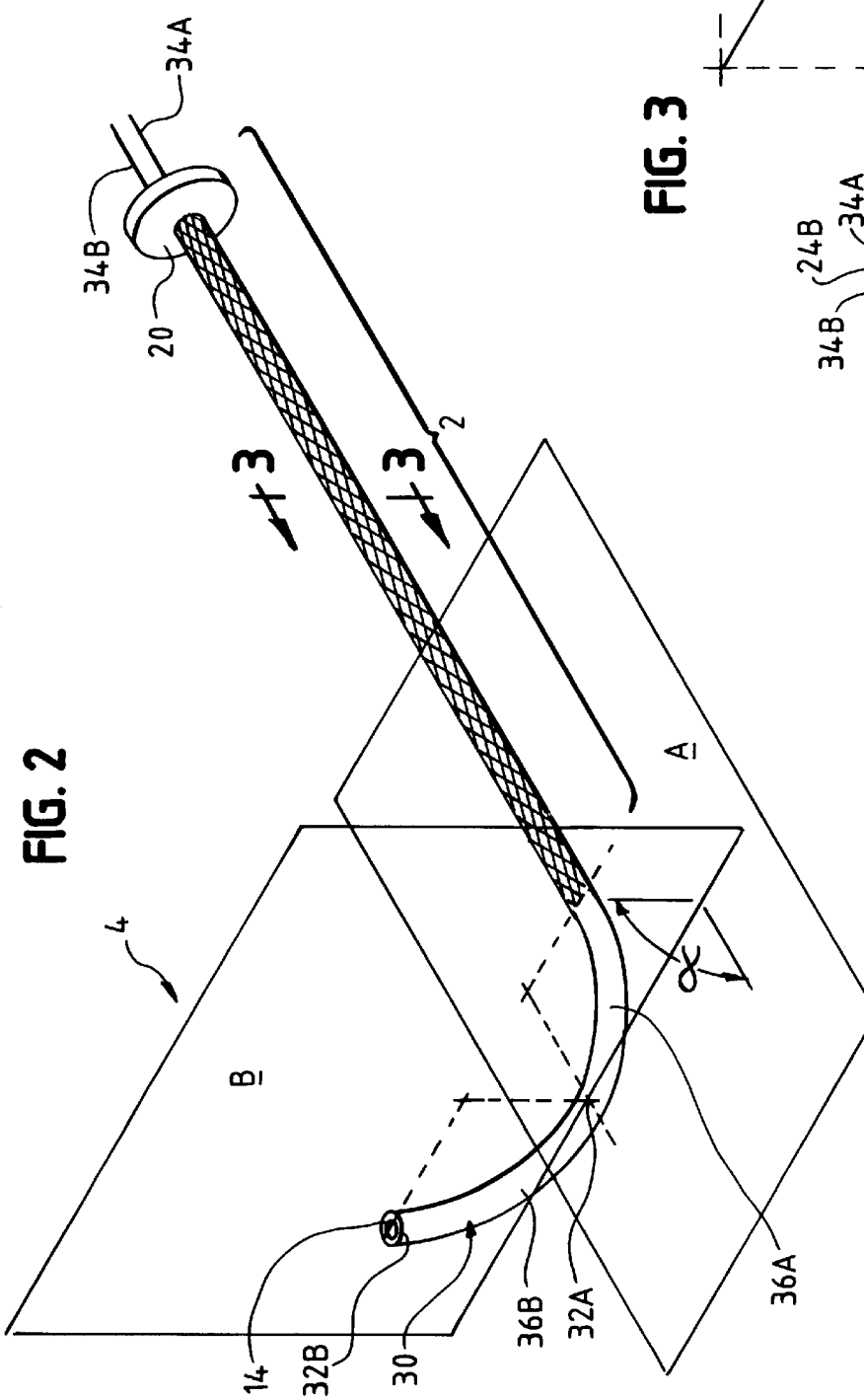

SELECTIVELY MANIPULABLE CATHETER

FIELD OF THE INVENTION

The present invention provides an improved catheter for use in medical applications.

BACKGROUND OF THE INVENTION

Catheters (including both standard catheters and so-called vascular sheaths) are used in a wide variety of medical procedures. For example, some catheters are used to reach selected sites within the human vasculature so that a drug can be delivered to a specific site. Alternatively, a second medical device, such as a stent or septal defect occlusion device, may be delivered to the desired location through the catheter.

Other catheters include the capability to perform additional functions. For example, balloon catheters can be inflated to perform angioplasty or temporarily or permanently occlude a vessel. Other catheters include optical systems to permit a physician to visualize a remote site within the body, such as in endoscopy.

One of the primary difficulties in using a catheter is properly positioning the catheter within the desired body channel or cavity. In positioning a catheter within a patient's vasculature, for example, the physician will typically guide a thin, relatively steerable guidewire into position adjacent the desired location and then urge the catheter over the guidewire. The catheter will ostensibly track the guidewire and can be placed in the desired location in that manner. If the guidewire is removed from the catheter, though, it is not uncommon for the distal tip of the catheter to become unseated from a desired location. This is believed to be due to an inherent restoring force of the catheter walls—upon removal of the constraint of the guidewire, the catheter will tend to return toward its natural, unstressed state and this spring force can pull the tip of the catheter out of a particular branch of a vessel.

Some catheters are guided into place without the use of guidewires. So long as the catheter has sufficient "pushability," i.e., can be urged distally from a proximal location without buckling or kinking, this can reduce the number of steps in deploying a catheter to a single procedure. Unfortunately, such guide catheters tend to be more difficult to steer into position and their stiffness necessarily limits their deployment in more tortuous vessels.

Both to help seat catheters in the desired location and to help physicians steer guide catheters without the use of a guidewire, a number of physicians have proposed shaping the catheter tip in a particular fashion. This does make it easier to deploy the catheter in one specific type of procedure. Unfortunately, each specific type of procedure will commonly have one or two optimized catheter designs which have less utility in other procedures. Accordingly, there has been a very rapid increase in the number of different catheter designs that hospitals must stock to provide their physicians with a suitable array of state-of-the-art catheters. The problem is made even more acute by the fact that differently sized patients will have differently sized vasculatures. Hence, even for a single catheter design for use in a single type of procedure, one may have to carry several different sizes to accommodate children, small adults and large adults.

One other disadvantage of pre-formed, off-the-shelf catheters is that they do not allow the physician to take into account any peculiarities of a patient's vascular system. Instead, physicians are expected to do the best they can with the off-the-shelf catheters. Some physicians choose to take a different approach and customize the catheter they intend to use in a procedure to meet the anticipated needs. Most catheters are formed of a thermoplastic material and can be reshaped to some extent when heated. A physician may, for example, heat a length of the catheter until it becomes maleable, then reshape the heated length. When it cools down, the catheter will retain at least some of the modified shape imposed while it was heated.

Such crude reconstruction after the fact, however, has its own problems. First, it is obviously relatively time-consuming and requires the physician to have more equipment in the operating theater. In addition, if the physician discovers during a procedure that the patient's vasculature is different from what was anticipated, the physician would either have to utilize a pre-formed catheter or would have to suspend the procedure while he or she shaped an appropriate catheter. Another problem with such manual reshaping is that it can, in some circumstances, compromise the lumen of the catheter. When a catheter is bent, particularly through more acute angles, the lumen will have a tendency to at least "ovalize," i.e., the generally circular lumen may flatten out to some extent, or even kink and effectively seal at a bend. Where high flow rates of fluid are necessary or when a medical device must be passed through the catheter, such ovalization or kinking can make the catheter virtually useless.

Some catheters and endoscopes can be remotely steered. For example, U.S. Pat. No. 5,325,845 (issued to Adair in 1994, the teachings of which are incorporated herein by reference) suggests a steerable sheath for use in connection with optical catheters. The proximal end of the catheter is provided with a pair of steering knobs which are connected to wires that run along the length of the catheter. Each knob controls a pair of diametrically opposed wires and all four of the wires are attached to the distal tip of the catheter. By appropriate manipulation of either of the control knobs, one can ostensibly control the position of the distal tip of the catheter. By such remote manipulation, the reference claims a physician can move the optical catheter into position to view the desired site.

Others have proposed similar uses of cables in endoscopic procedures. For example, U.S. Pat. No. 4,700,693 (issued to Lia et al., in 1987, the teachings of which are incorporated herein by reference) suggests a design which utilizes steering cables and a number of washers. The steering cables can be remotely manipulated to guide the endoscope through a desired curve.

SUMMARY OF THE INVENTION

The present invention provides an improved catheter system which allows a physician to shape a length of the catheter to permit it to be more readily positioned within a body channel of a patient. One preferred embodiment of the invention provides a remotely steerable catheter which can be manipulated by a physician even after the catheter is placed into the patient's body. In this embodiment, the catheter includes an elongate tubular member which has a proximal end, a distal end, a remotely manipulable length, and a wall defining a lumen. The catheter also includes first and second wires slidably retained by the wall and extending proximally beyond the proximal end of the tubular member. The first wire is attached adjacent a distal end thereof to the wall at a first node located along the manipulable length. The second wire is attached adjacent a distal end thereof to the wall at a second node located along the manipulable length, with the second node being located distally of the first node along the manipulable length of the tubular member. If so desired, one or both of the first and second wires can be slidably received within the wall of the tubular member, such as within dedicated channels in the wall.

Another embodiment of the invention provides a selectively formable catheter. As in the preceding embodiment, this catheter includes an elongate tubular member having a proximal end, a distal end, a selectively formable length, and a wall defining a lumen. However, this embodiment of the invention provides a distal locking segment and a proximal locking segment carried by the wall of the elongate tubular member and located along the selectively formable length of that member. The proximal and distal segments are selectively moveable between an unlocked position wherein the locking segments are free to pivot with respect to one another and a locked position wherein the locking segments are constrained against relative movement. If so desired, the catheter can also include at least one control wire retained by the wall of the elongate tubular member, with the control wire extending proximally from the distal locking segment to a location proximal of the proximal locking segment. This will permit one to remotely engage the locking segments in their locked position.

BRIEF DESCRIPTION OF THE DRAWINGS

FIG. 1A is a schematic view in partial cross section of an embodiment of the catheter of the invention;

FIG. 1B is a schematic elevation view of the catheter of FIG. 1A curved for manipulation within a patient's vascular system;

FIG. 2 is a schematic perspective view of a catheter in accordance with the invention having two curves lying in different planes;

FIG. 3 is a proximal cross sectional view of the catheter of FIG. 2 taken along the line 3—3 in FIG. 2;

DETAILED DESCRIPTION OF THE PREFERRED EMBODIMENTS

Figure 4:
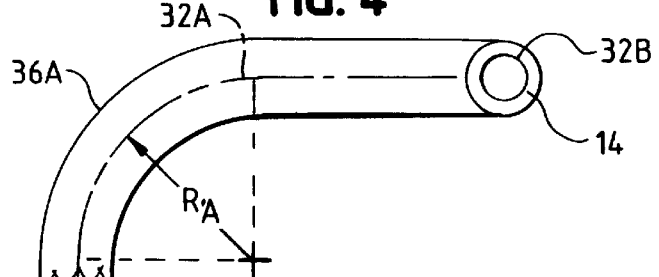
FIG. 4 is a top elevational view of the catheter of FIG. 2 taken along a line of sight represented by the arrow in FIG. 2.

FIGS. 1A and 1B schematically illustrate the basic structure and capabilities of a catheter 10 in accordance with the present invention. The catheter 10 is generally tubular in shape and desirably includes at least one lumen 12. As is known in the catheter art, it may be desirable to provide more than one lumen or to subdivide a large lumen into two or more separate lumens, such as in balloon angioplasty.

The catheter extends from a proximal end 20 to a distal end 14. The catheter can be thought of as having at least two separate regions, namely a proximal length 22 and a formable length 30. If so desired, a distal length 16 may extend distally beyond the distal end of the formable length. Such a distal length may be used to provide a relatively soft a traumatic tip on the catheter.

The overall length of the catheter may be varied as necessary. For some procedures, the catheter can be fairly short as the distance between the insertion point into a patient's vessel and the target site is relatively short. In other circumstances, the catheter may be required to traverse a relatively long path, such as in reaching a remote site in a patient's vasculature. Accordingly, depending on the class of procedures for which the catheter is intended, the length can vary considerably. However, typical catheter lengths will be on the order of about 50–150 cm, with the range being narrower for catheters intended to access a particular region. For example, abdominal and renal catheters are typically on the order of about 50–70 cm while intracranial catheters are usually longer, with lengths of about 100–125 cm being most common.

The relative lengths of the proximal length 22, formable length 30 and distal length 16 can also vary significantly depending on the application for which the catheter is intended. Typically, though, the proximal length 22 will comprise a majority of the catheter's length. For example, in a catheter which may be useful in selective cerebral angiography, the catheter may be about 5 French to about 6 French and have a total length of about 100–110 cm, with a proximal length 22 of about 60–80 cm and the balance comprising the formable length. If a distal length 16 is provided extending distally beyond the end of the formable length, such a distal length is optimally kept fairly short, e.g. 1 cm or less. It should be understood, though, that the formable length 30 may extend substantially from the proximal end 20 to the distal end 14 of the catheter, i.e., the catheter need not have a separate and distinct proximal length 22 or distal length 16.

FIGS. 1A and 1B schematically illustrate the ability to manipulate the formable length 30 into a useful shape. The formable length includes a plurality of links 40 (shown schematically in FIG. 1A). The structure of these links is discussed in more detail below, but each link 40 has a lumen 42 and is movable with respect to the adjacent links. In particular, each link can be pivoted with respect to the adjacent link or links so the catheter can be curved. The links help define a patent lumen 12 of the catheter along the manipulable length 30 while permitted the manipulable length of the catheter to be bent into the desired configuration and, at least in one embodiment, maintain that shape.

FIG. 1B shows the catheter 10 of FIG. 1A bent into one particular shape. The shape which a physician may choose for the catheter will vary depending on the nature of the procedure for which the catheter is being used. In some circumstances, only a single curve along a distal portion may be necessary (as in the well-known J-tip catheters), while in other procedures more complex curvatures may be necessary to readily reach the desired site. The shape shown in FIG. 1B is essentially random and is chosen solely for purposes of illustration of the benefits of the present design.

The formable length 30 in FIG. 1B extends along four different arcs of curvature. The first arc 36A extends from the proximal end of the manipulable length 30 to the first node 32A. The second arc 36B extends from the first node 32A to the second node 32B. The third arc 36C extends from the second node 32B to the third node 32C. The fourth arc 36D extends from the third node 32C to the fourth node 32D.

Each of these arcs in FIG. 1B has a different radius of curvature and, to make the drawing clearer for purposes of discussion, each arc curves in a different direction from the two adjacent arcs.

Depending on which embodiment of the invention is employed, the shape of the catheter between the nodes can be varied either by remote manipulation using control wires 34 or by forming the formable length 30 into the desired shape before inserting the catheter into the patient's vessel.

In the embodiment shown in FIGS. 1A and 1B, a plurality of control wires 34 are provided. In particular, there is a separate control wire provided for each node. Each of these control wires has a proximal end which extends proximally beyond the proximal end of the catheter, as shown on FIG. 1A. This allows an operator to manually grasp the control wires to manipulate the catheter.

In order to allow a physician to more readily determine which of the four wires is to be grasped, each of the wires, or at least a proximal length of each of the wires, can be provided with a different color. Although this can be accomplished by making the wires themselves out of a colored material, it may be more practical to accomplish this end by providing a metal control wire for tensile strength and simply coat the wire with a colored coating. If so desired, the entire length of the wire may be coated with a low-friction material such as polytetrafluoroethylene and the color component can be added to that coating.

Each of the control wires extends along the length of the catheter until the proximal end of the control wire reaches a particular node. In some embodiments, it may be useful to provide more than one wire at any given node. By spacing these wires about the circumference of the catheter, one can change the nature of the curvature along an arc extending up to that node. Such a basic approach is mentioned in Adair's U.S. Pat. No. 5,325,845, incorporated by reference above. In that design, four different wires are all attached to the distal end of the catheter, permitting the tip to be bent through a single curve in any desired direction.

In the embodiment illustrated in FIGS. 1A and 1B, though, each of the four control wires is attached to a different node. In particular, control wire 34A is attached to node 32A; control wire 34B is attached to node 32B; control wire 34C is attached to node 32C; and control wire 34D is attached to node 32D. As these nodes are spaced from one another along the length of the catheter, the control wires will extend a different length along the length of the catheter before reaching the associated node.

Each node in the catheter of the invention will comprise one or more of the links 40. In the embodiment illustrated in FIG. 1A, each node simply comprises a single link 40' to which one of the control wires is physically attached. The control wires can be attached to their associated links in any suitable fashion. For example, they can be bonded by welding, brazing, or soldering, by a suitable biocompatible adhesive, or by a less secure mechanical link. As described below, the primary purpose of the control wires is to allow the operator to urge proximally on a specific link. Accordingly, a control wire 34 need not be physically attached to its link 40'. For example, one could provide a proximally facing shoulder on the distal end of the control wire and a distally facing shoulder on the associated link, permitting the control wire to be in controllable contact with the associated link, whereby the control wire can move with respect to the link when the wire is not under tension.

In light of the lumen 42 running through each of the links, the links have a generally annular shape. (This shape can take on a number of substantially different variations, as suggested by FIGS. 5–9 and discussed in more detail below.) As the axis of the links are open, the control wires will be attached to the associated link 40" at a location spaced away from the link's axis. Pulling proximally on the wire, therefore, will exert an uneven force on the link, tending to pull just one side of the link proximally.

Each of the control wires desirably extends along the catheter between the proximal end and the point at which it is attached to a link 40' at a node 32. Pulling proximally on the control wire will tend to compress one side of the catheter without compressing the other. As described more fully below, the links are attached to one another in such a fashion as to permit them to pivot with respect to one another while maintaining their respective lumens 42 in fluid communication with one another. As a matter of fact, depending on how the links are joined in the formable length, the side opposite the control wire may even be placed under tension, as noted below.

The compressed side of the catheter will be shorter than the opposite side, lending a degree of curvature to the catheter. The more one is able to compress one side of the catheter as compared to the opposite side, the smaller the radius of curvature of that length of the catheter will be.

The principles of this concept are best understood with reference to the schematic drawing of FIGS. 1A and 1B. In FIG. 1A, the manipulable length 30 of the catheter 10 is shown as being substantially straight, with all of the links directly aligned with one another. By applying proximal tension on the control wire 34, though, the formable length 30 of the catheter is deformed into a series of arcs, as noted above.

The control wire 34A is attached to the link 40' at node 32A. This control wire 34A extends generally along the bottom side of the catheter in FIG. 1A. (For purposes of clarity, only control wires 34A and 34B are shown extending along the catheter in the schematic cross section of FIG. 1A, but it should be understood that the other two wires 34C and 34D would also be seen in a true cross section.) By pulling proximally on control wire 34A, the bottom side of the catheter in FIG. 1A will be compressed while the upper side of the catheter will either stay about the same or expand somewhat under tension. As a result, the portion of the formable length 30 of the catheter extending from the proximal length 22 to the node 32A will tend to deflect downwardly. This is illustrated as arc 36A in FIG. 1B.

Control wire 34B is attached to the link 40' at the second node 32B and extends along the upper side of the catheter shown in FIG. 1A. Accordingly, pulling proximally on the wire 34B will tend to cause the formable link of the catheter to deflect upwardly. If there is no tension on the control wire 34A, this can cause the formable length 30 to curve upwardly from its proximal end adjacent the proximal length 22 to the second node 32B. If the tension on the control wire 34A is maintained, though, the first arc 36A will tend to curve downwardly and the control wire 34B will cause the arc 36B to curve upwardly primarily beyond the node 32A. In much the same manner, the arcs 36C and 36D can be formed by pulling proximally on the control wires 34C and 34D, respectively.

The schematic illustrations of FIGS. 1A and 1B are simply rough schematic depictions of the invention, but they do illustrate one of the fundamental advantages of the invention—providing the ability to form a catheter into a relatively complex shape without undue effort. If any one or more of the arcs illustrated in FIG. 1B are not necessary to achieve the desired shape, such an arc may be decreased or omitted by reducing the tension on the associated control wire 34.

For example, one could provide the formable length 30 of the catheter with a single long, gradual curve by pulling only on control wire 34D. Without the tension applied to the other three control wires 34A–34C, the compressive force of the control wire 34D will tend to act along the entire formable length 30 of the catheter, yielding a single, simple curve. The more tension one applies on the wire 34D, the more acute that curve will become. If a more complex shape is needed, one can simply retract one or more of the other control wires to yield the most suitable shape to meet the needs at hand.

As noted above, the shaping of the catheter relies on relative compression of portions of the catheter with respect to opposed sides of the catheter. To allow more precise control of the shape of the formable length, it is preferred that the proximal portion 22 have relatively high column strength. A number of techniques are known in the art for improving the column strength (often referred to as "pushability") of a length of catheter and such techniques need not be discussed in detail here. Two common ways to accomplish this end, though, are to incorporate a tubular braid into the wall of the catheter, as illustrated schematically in FIGS. 1–4, or to form the length of catheter of a higher durometer plastic material.

FIG. 1B illustrates one of the more intriguing advantages of a catheter of the invention. In prior designs which are capable of remote manipulation (such as Adair's U.S. Pat. No. 5,325,845, incorporated by reference above), the catheter can only be bent through a single curve by manipulating a wire or a series of wires. This is because all the wires terminate at the same point along the length of the catheter. In Adair's design, four different control wires are provided. However, they are all attached to the distal end of the steerable sheath. As a result, the distal tip can be moved in any desired direction, but it is impossible to form complex curves.

By terminating the control wires 34 at nodes spaced from one another along the length of the formable length 30 of the catheter 10, one can achieve a much more complex curvature with the same number of control wires employed by Adair. As a result, one can form the catheter into a shape optimized to follow a tortuous path in the patient's vessel to properly position the distal end 14 of the catheter.

In the illustration on FIG. 1B, the entire catheter lies in the plane of the paper. However, the present invention is not limited to curvatures in a single plane. The ability to curve the catheter in multiple planes is illustrated in FIGS. 2–4. FIG. 2 is a perspective view of a catheter having two distinct arcs 36A and 36B, each lying in a different plane. FIG. 3 provides a cross sectional view of the catheter of FIG. 2 taken along line 3—3 in FIG. 2 and looking distally toward the distal end 14 of the catheter. FIG. 4 illustrates a view of the catheter of FIG. 2 from above, illustrated schematically by the arrow 4 in FIG. 2.

The structure of the catheter shown in FIG. 2 is very similar to the structure of the catheter 10 of FIGS. 1A and 1B. It is interesting to note, though, that the distal length 16 has been omitted in the catheter 10 of FIG. 2. Instead, the distal end of the formable length 30 is also the distal end of the catheter.

The first arc 36A extends from the proximal end of the formable length 30 to the first node 32A. The axis of the catheter along this arc 36A lies essentially entirely within the plane A shown in FIG. 2. The second arc 36B of the catheter extends from the first node 32A to the second node 32B. The axis of the catheter along this second arc 36B lies essentially entirely within the plane B in FIG. 2. This drawing is somewhat schematic in nature. As a result, there is a very sharp demarcation between the arc 36A and the arc 36B. Similarly, the entire length of the arc 36A lies entirely within the plane A and the entire length of the arc 36B lies in the plane B. In reality, such a clear, precise demarcation is somewhat unlikely. In particular, the first curve 36A may curve upwardly somewhat along its length, deviating from the plane A, due to the tension on the control wire 34B.

The degree of curvature of the two curved sections 36A and 36B can be controlled by the tension placed on the associated control wire 34. As best seen with reference to FIGS. 3 and 4, the control wires 34A and 34B are spaced from one another about the circumference of the wall of the catheter by about 90 degrees. Turning first to FIG. 4, pulling proximally on the wire 34A will tend to compress the right side of the catheter in that drawing, causing it to deflect to the right. The harder the operator pulls proximally on the wire 34A, the smaller the radius of curvature $R_A$ of the arc 36A will become. Turning to FIG. 3, when an operator pulls the control wire 34B proximally, it will tend to compress the top of the catheter in that view, causing the catheter to deflect upwardly. Applying more tension to the control wire 34B will tend to reduce the radius $R_B$ of the arc 36B.

The angle between the two planes in which the two curves lie (A and B in FIG. 2) will depend on the angular spacing of the two control wires about the circumference of the wall of the catheter. As suggested in FIGS. 3 and 4, spacing the control wires 34A and 34B about 90 degrees from one another will provide curves in two generally perpendicular planes (assuming the curve 36A lies in a plane because any deflection of the curved section 36A out of its plane will apply tension on wire 34B along the section 36A). By changing this spacing, though, one can change the angle between these two planes (designated as $\alpha$ in FIG. 2).

FIGS. 2–4 illustrate a catheter which is bent through just two arcs 36A and 36B. It should be understood, though, that the catheter can include many arcs. For instance, the control wires 34A–34D in FIG. 1B all lie in the plane of that figure, with two lying on one side of the catheter and two lying on the other side. (As noted above, only control wires 34A and 34B are shown along their full lengths; if shown, wire 34C would lie immediately adjacent wire 34A and wire 34D would lie immediately adjacent wire 34B.) If the control wires were spaced differently about the wall of the catheter, the catheter could be made to curve in as many as four different planes rather than in the single plane shown in FIG. 1B.

The control wires 34 may extend along the catheter in any suitable location. The control wires can extend along the exterior of the catheter, perhaps having retaining loops to keep them in place on the catheter wall in a fashion similar to the use of guide loops along a fishing rod to keep the fishing line along the rod. However, that is not optimal because it is generally desirable to have a catheter with a relatively smooth outer wall to make it easier to advance within a vessel and to reduce trauma to the intima of the vessel.

One could instead have the control wires 34 extend within the lumen of the catheter, with each of the wires being attached adjacent its distal end to the lumen of its associated link 40'. This may suffice if the catheter is to be used solely to deliver a fluid or if the control wires are retained within a separate lumen and a second lumen is provided, e.g.

having a separate lumen for balloon dilatation. However, if a second device is to be delivered through the catheter, having that device and the control wires in the same lumen runs the risk of getting the wires entangled with the device, either damaging the device or limiting the ability to remotely shape the catheter 10.

FIG. 3 shows one preferred embodiment which avoids these pitfalls by enclosing the control wires 34 within the wall of the catheter 10. In this drawing, it can be seen that the control wires 34 are received in separate wire lumens 24 in the proximal section of the catheter, with wire 34A being received in wire lumen 24A and wire 34B being received in wire lumen 24B. These lumens may be formed by using an appropriate die in an extrusion process. The proximal length 22 can instead be made of more than one layer; multi-layer constructions are common when incorporating a tubular braid, with the braid being sandwiched between two separately extruded lengths of tubing which are then bonded to one another and/or to the braid, e.g. by an adhesive. In such a design, elongate spacers can be provided along the length of the catheter before the two layers are assembled, with the spacers being spaced from one another to define elongate channels in the body of the proximal length 22. Other ways of forming these channels will also be readily apparent to one of ordinary skill in the art and need not be discussed in detail here. One or more wires can be received in and slide longitudinally within each of these channels.

As discussed in more detail below, the links 40 optimally are provided with wire lumens 44 within which the control wires are slidably received. This, in combination with the wire lumens 24 in the proximal length 22, will permit the control wires to be moved with respect to the wall of the catheter within which they are enclosed so the catheter can be manipulated.

The above discussion has focused on an embodiment employing control wires to manipulate the catheter. Allowing a physician to control the shape of the catheter from a proximal position is particularly advantageous because it enables the physician to manipulate the catheter during the course of a procedure. For example, if angiograms from several different sites need to be taken, one need not use a separate, specially shaped catheter for each angiogram. Instead, the catheter can remain in the patient's body and be reformed into a different optimized shape to reach each of the different sites. The same capabilities can also allow a physician to adapt the shape of the catheter to meet actual conditions when a patient's vasculature differs from the anticipated shape or condition.

However, utilizing a series of control wires 34 adds to the complexity of the design. If so desired, such control wires can be omitted and the catheter can be manipulated into the desired shape before the catheter is placed in the patient's body. Although the physician will no longer be able to change the shape of the catheter as readily during the middle of a procedure, the ability to shape a single, standardized catheter into the needed shape before use can greatly reduce the number of differently shaped catheters a hospital or other facility would need to keep in inventory to assure an adequately stocked operating theater.

In such an embodiment, links along the formable length would be adapted to lock to one another on one or more sides. (One possible mechanism for locking adjacent links to one another is discussed below in connection with FIG. 5.) Before the catheter is to be deployed in a patient's body, the physician can determine the shape he or she believes is needed and can manipulate the formable length 30 into such a configuration. Bending the formable length will urge one side of two adjacent links toward with one another until the links are locked together on that side. This will set that curvature at that point along the length of the catheter unless or until the links are unlocked (a mechanism for which also is discussed below).

By so locking links to one another along the formable length of the catheter, the physician can define a desired shape for such a catheter on a case-by-case basis. This will greatly enhance the versatility of the catheter, permitting it to be optimized for a variety of different procedures, without unduly increasing the complexity and cost of the catheter. Hence, though this embodiment may lack some of the capabilities of the embodiment discussed above utilizing control wires for remotely shaping the formable length of the catheter, it can still provide advantages over current catheter designs.

It is preferable that at least one wire extend along the length of the formable length and, ideally, extends from a position adjacent to the distal end 14 of the catheter proximally beyond the proximal end of the catheter. This will improve the safety of the device by maintaining a physical connection to the distal end of the device. This way, if the catheter catastrophically fails and a distal segment thereof breaks free, the wire will keep the separated distal segment from drifting within the patient's vascular system and embolyzing a vessel downstream. If one or more control wires 34 are employed, the distal-most control wire can serve this function. If the control wires are omitted entirely, it is still desirable to have a safety wire, though. Since such a safety wire need not be moved to apply tension as in the case of the control wires 34, the safety wire can simply be imbedded in or otherwise attached to the wall of the catheter.

FIGS. 5–9 illustrate a few possible link designs for use in a formable length 30 of a catheter 10 of the invention. Turning first to the embodiment shown in FIGS. 5 and 6, each link 40 has a distal section 50 and a proximal section 60. These sections may be integrally formed of a single material, such as by injection molding the link from a plastic material.

An elongate central lumen 42 extends through the entire length of the link, desirably generally centered along the axis of the link. The distal section 50 includes a tubular length 52 which desirably extends proximally from the distal end of the link and merges into a distally-facing shoulder 54. This shoulder extends from the outer diameter of the distal length 52 of the distal section out to the larger outer diameter of the proximal section 60. Although this shoulder may be perpendicular to the axis of the link, providing a sharp increase in diameter, it is preferred that the shoulder taper more gradually from the distal length 52 to the proximal section 60. This yields a shoulder 54 which extends outwardly at an obtuse angle with respect to the distal length 52 as shown in the drawings.

Figure 5:
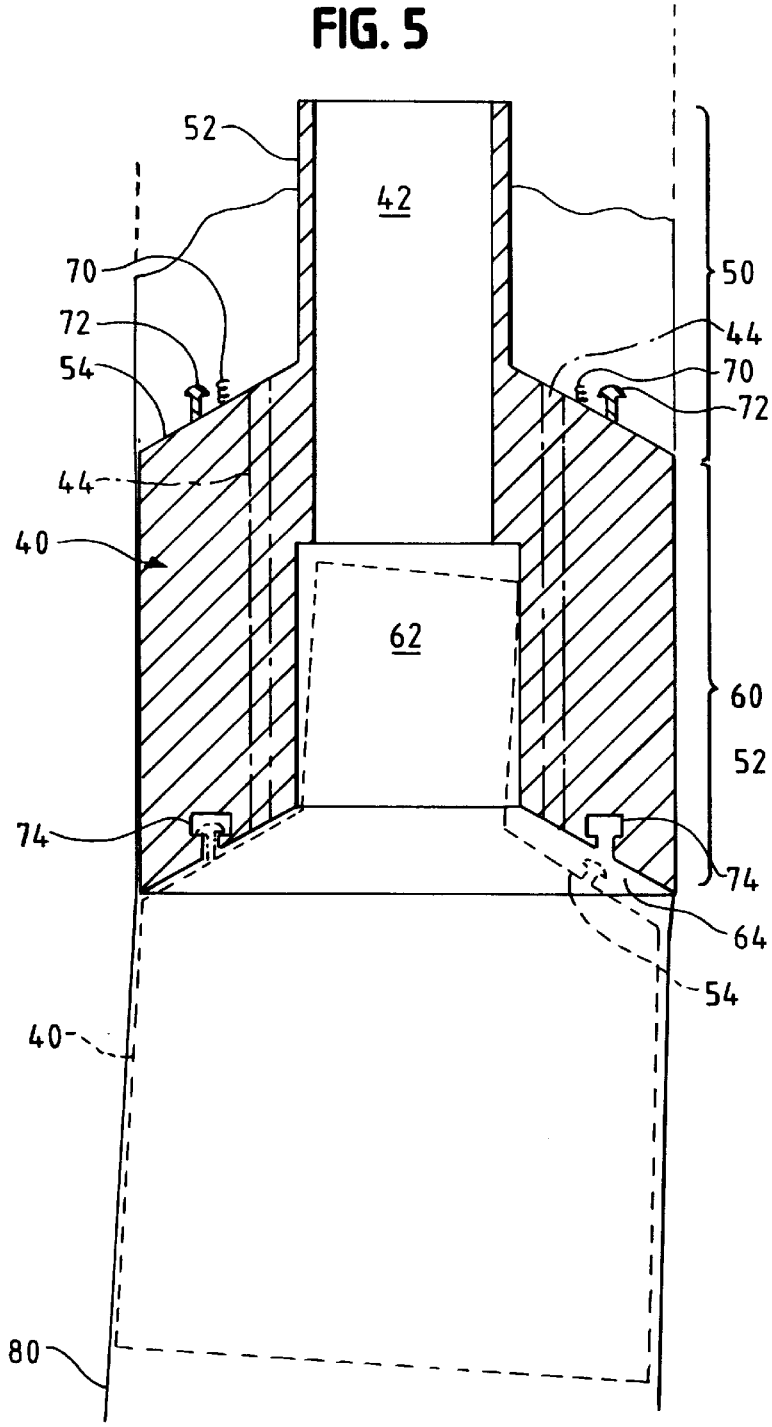
FIG. 5 is a cross-sectional view schematically illustrating one link and its relationship to another link in a manipulable length of a catheter of the invention.

The proximal section 60 includes an enlarged recess 62 therein and a proximally facing shoulder 64. The enlarged recess 62 should be sized to receive therein the distal length 52 of the distal section of another link 40 (shown in phantom lines in FIG. 5). Optimally, the recess is larger than the distal length 52' which it receives, both in terms of length and in inner diameter. As illustrated in FIG. 5, this will permit the distal length 52 to turn within the recess 62 so the relative angular positions of the links can be adjusted while keeping the distal length 52 in the recess 62. This retention is important in that it will help ensure that the separate lumens 42 of the links stay in fluid communication with one another to ensure that the lumen 12 of the catheter remains patent along the formable length 30.

Figure 6:
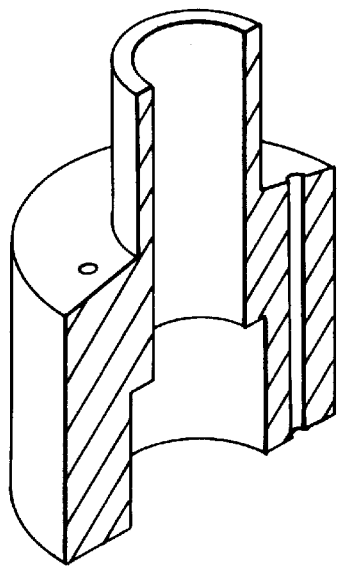
FIG. 6 is a perspective cross-sectional view of one of the links of FIG. 5.

The proximally-facing shoulder 64 shown in FIGS. 5 and 6 tapers outwardly from the recess 62 to the outer diameter of the proximal section 60. The angle of this taper can be varied and, in many circumstances, it may be better to have a much sharper shoulder. In particular, the shoulder may meet the interior surface of the recess at a 90° angle, or even an acute angle, rather than the obtuse angle shown. This will leave more room for the proximal link to move with respect to the distal link without abutting the distally-facing shoulder 54 of the proximal link against the proximally-facing shoulder 64 of the distal link, increasing the freedom to pivot one link with respect to another and create more acutely curved arcs.

In the illustrated embodiment, though, it is preferred that the angle between the proximally-facing shoulder and the interior surface of the recess be slightly smaller than the angle between the distal length 52 and the distally-facing shoulder 54. This will permit these two shoulders to abut one another on one side of the two links when the links are pivoted with respect to one another. This will, in turn, allow the links to be locked to one another on this side, locking in the curvature of the catheter 10 at that location.

The link of FIG. 5 is specifically adapted to allow two links to lock to one another. (The locking components of FIG. 5 are omitted from FIG. 6 both for purposes of clarity and to illustrate that they are not necessary for the effective operation of the link.) The link may be provided with at least one spring 70 to urge links apart from one another. This is typified in FIG. 5 as a series of compressive coil springs 70 carried at locations spaced about the distally-facing shoulder 54. Instead of using a series of discrete springs, though, it is more likely that a resilient ring will be placed between the links. This can even be accomplished by molding a suitable elastomeric material into the gap between adjacent links when forming the sleeve 80, discussed below.

In addition to the springs, each of the links of FIG. 5 include at least one locking pin 72 extending distally from the distally-facing shoulder 54. The heads of these locking pins 72 are sized to be received in a locking recess 74 in the proximally-facing shoulder 64 of another link. When the head of a locking pin is urged into a locking recess 74, the head of the pin will deform and resiliently expand into the recess, holding the pin in place. This can be a one-way, irreversible process, much like a permanent press-fit. This is particularly useful in the embodiment of the invention where the catheter is to be formed before insertion into the patients' body and there is no need to further manipulate the shape of the catheter during use.

Alternatively, the head of the locking pin 72 may be retracted from the locking recess 74, making the locking of two links to one another reversible. In this event, the force necessary to retract the head of the pin from the recess in which it is received can be provided by the force of the spring 70. This can work quite well in the case of catheters employing one or more control wires 34 as the control wires can supply the force needed to act against the spring 70 and keep the links locked together. Such a reversible locking arrangement may be less desirable, however, in the alternative embodiment discussed above which omits any control wires 34.

FIG. 5 illustrates how two adjacent links can be positioned with respect to one another when the catheter is bent through an arc. The distal segment 52 of the proximal link (shown in phantom lines) is at an angle within the enlarged recess 62 in the distal link. This places the axis of the distal link at an angle to the axis of the proximal link.

The difference is best seen in the relative positions of the shoulders of the two links on opposed sides. On the right side of FIG. 5, the distally-facing shoulder 54 of the proximal link is immediately adjacent the proximally-facing shoulder 64 of the distal link. On the left side of FIG. 5, the distally-facing shoulder of the proximal link is immediately adjacent the proximally-facing shoulder of the distal link. As a matter of fact, the locking pin 72 of the proximal link is received within the locking recess 74 of the distal link on the left side, locking the two links together in this orientation.

Although the angle between the two links in FIG. 5 is not large, the maximum angle between adjacent links can be increased by appropriately modifying the relative dimensions of some of the elements (especially the outer diameter of the distal length 52 and the inner dimensions of the recess 62 and the angular orientation of the two shoulders 54, 64). Furthermore, the angle between two adjacent links need not be large to yield acceptable curvature of the catheter. As a matter of fact, if the links are small, i.e. the number of links per unit length is large, the angle between adjacent links can be less while still producing an arc of a relatively small radius.

If so desired, the formable segment 30 of the catheter can be encased in a flexible sheath 80. The sheath is desirably formed of a flexible plastic material so the links can pivot within the sheath. To ensure that the links define the shape of the formable length 30 more so than does the sheath, the links are desirably formed of a stiffer material than is the sheath. While the links can be formed of metal, it may be substantially cheaper and easier to form more complex links out of a plastic material. So long as the plastic material of the sheath is less stiff than the plastic of the links, though, this should not present any problem. The sheath can be formed of any suitable biocompatible material. Low-friction, heat-shrinkable materials are preferred and polytetrafluoroethylene is believed to be suitable for this purpose.

Such a sheath can provide a number of advantages. First, while adjacent links 40 may be in fluid communication with one another, there need not be (and generally will not be) a fluid-tight seal between adjacent links. Encasing the links in a sheath 80 can help seal the catheter, permitting one to inject contrast media or the like through the catheter at higher delivery rates. The spaces between adjacent links creates an irregular surface, especially when the catheter is bent through an arc. An outer sheath 80 can provide a smoother outer surface, reducing trauma to the lining of the vessel in which it is deployed. In addition, if the sheath is formed of a low-friction material such as polytetrafluoroethylene, the sheath will make it easier to slide within the vessel for placement.

The embodiment illustrated in FIG. 5 does not include a sheath lining the lumen 42 of the links. If so desired, though, such a sheath may be provided in that lumen either instead of or in addition to the outer sheath 80. An inner sheath would also serve to seal the lumen 12 of the catheter along the formable length, further enhancing fluid delivery rates through the catheter.

As noted above, the links 40 of the invention desirably include control wire lumens 44 extending therethrough. These control wire lumens can extend generally parallel to the axis of the link 40, as shown in FIGS. 5 and 6, for example. By properly aligning the control wire lumens of the series of links, one can define a relatively straight path for the control wires to follow (at least when the catheter is not curved).

These lumens should be spaced angularly about the proximal section 60 of the link to yield the desired planes of curvature, as discussed above in connection with FIGS. 2–4. For example, these lumens can be spaced equiangularly about the proximal section 60. In any event, it is likely that the control wire lumens will be spaced from one another at least about 45°. This will yield a series of arcs, each of which may extend substantially in a single, fairly flat plane.

The path of the wire lumens 44 through each link need not be straight, however. In an alternative embodiment (not illustrated), the wire lumens are oriented at an angle with respect to the axis of the link. While the proximal and distal ends of the wire lumens 44 desirably are both the same distance from the axis, the distal end can be angularly displaced from the proximal end. For example, each of the wire lumens may take a helical path through the link and curve about 30° along their respective lengths. The wire lumens of adjacent links would still be able to line up with one another, but the control wire 34 would take a helical path through the links. When the control wire is retracted to curve the catheter having such links, the curve of the catheter will not lie in a single plane, but the catheter will instead tend to curl somewhat as it curves. This can be particularly useful for the distal-most portion of the formable length 30 of the catheter.

In the above discussion, it was assumed that all of the links 40 in the formable length 30 would have the same construction. As discussed above in connection with FIGS. 1A and 1B, though, not all of the control wires will extend along the entire formable length 30. Hence, the distal-most links (those distal of the third node 32C) may have only one control wire (34D) extending through them while the proximal-most links (those proximal to the first node 32A) will have all of the control wires extending therethrough. Once the wire(s) occupying a given wire lumen terminate distally, there is no need for that lumen in more distal links. Accordingly, more distal links can have fewer wire lumens, with the distal-most links having only a single wire lumen. However, it likely will be cheaper to produce all of the links the same and simply leave one or more lumens unused in the more distal links.

Figure 7:
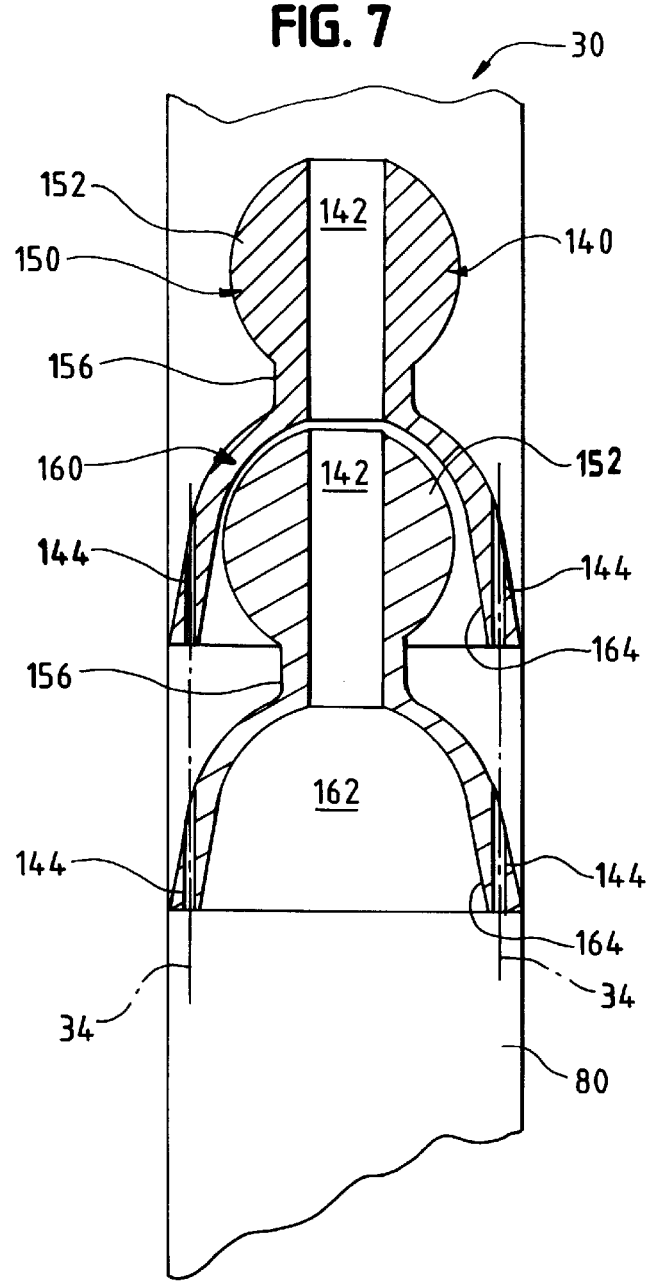
FIG. 7 is a schematic, cross-sectional view showing a different embodiment of a link for use in a catheter of the invention.

FIG. 7 illustrates an alternative embodiment of the link for use on a formable length 30 of a catheter of the invention. Elements in the link 140 of FIG. 7 which are functionally similar to elements in FIG. 5 bear like reference numerals to those used in FIG. 5, but incremented by 100 (e.g. link 40 in FIG. 5 is functionally similar to link 140 in FIG. 7).

The primary difference between these two links designs 40 and 140 lies in the nature of the interface between adjacent links. Whereas the distal length 52 of the link 40 of FIGS. 5 and 6 is straight and tubular in shape, the distal length 152 of the link 140 in FIG. 7 is generally spherical in shape. Similarly, the enlarged recess 62 in FIGS. 5 and 6 is generally cylindrical, but the distal portion of the recess 162 in FIG. 7 is hemispherical, with a diameter slightly larger than the diameter of the spherical distal length 152. This permits more freedom of movement from one link to the next, permitting a smaller radius of curvature with the same number of links.

The outward taper of the proximal portion 164 of the link should be chosen to restrict the links from pivoting sufficiently to allow their lumens to become completely misaligned and occlude the lumen 12 sufficiently to prevent passage of a fluid, a guidewire, or any other implement the catheter is intended to pass. The link 140 may be provided with a neck 156 extending between the proximal and distal sections (160 and 150, respectively). The length of this neck can also be used to control when the proximal section of one link strikes the proximal end of the next distal link to limit the angle one link may pivot with respect to another.

Figure 8:
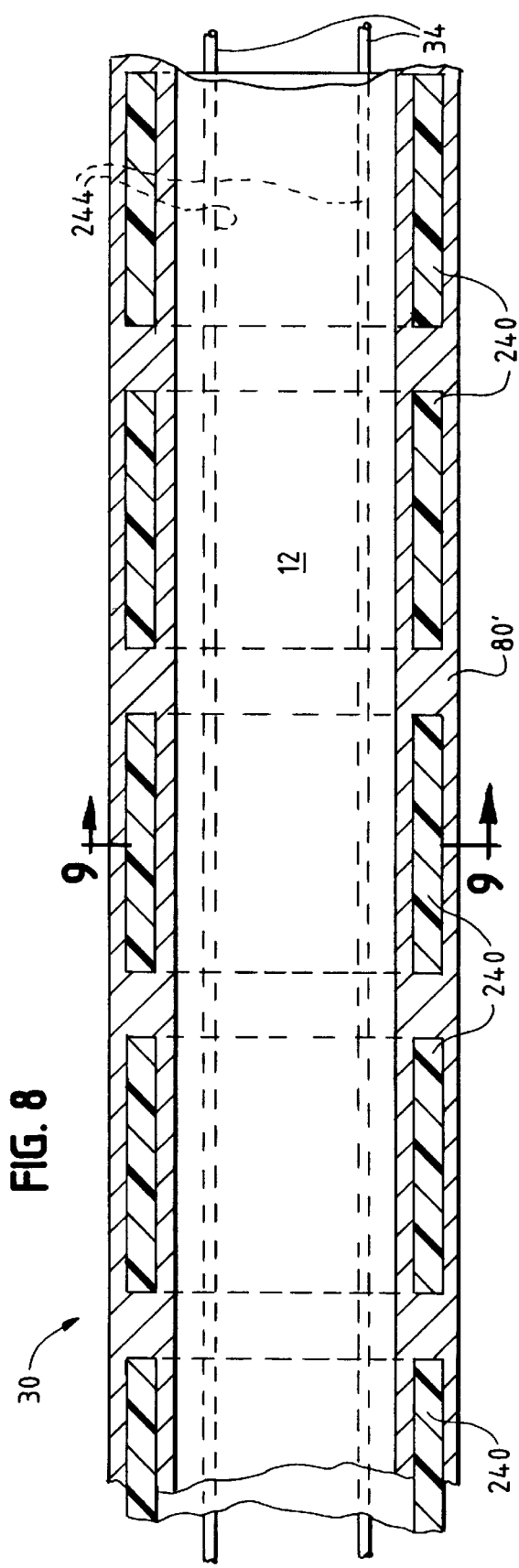
FIG. 8. is a cross-sectional view of a manipulable length of an alternative embodiment of the invention.
Figure 9:
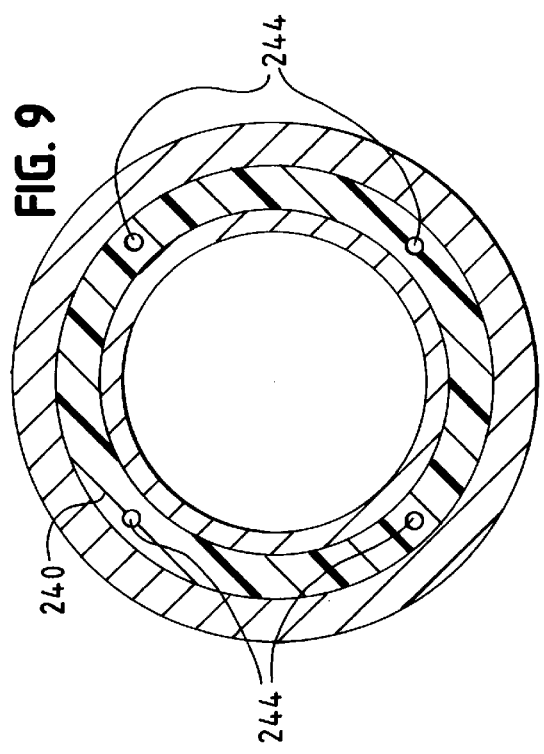
FIG. 9 is a cross-sectional view of the catheter of FIG. 8 taken along line 9—9.

FIGS. 8 and 9 illustrate another alternative embodiment of the invention. In each of the previous designs, the links are each adapted to mate with one another in some fashion. In the embodiment of FIGS. 8 and 9, however, the links 240 are spaced from one another along the manipulable length 30 of the catheter. Instead of having an external sheath 80, which may be relatively thin and add little to the structural integrity of the catheter, the links 240 in this design optimally are imbedded in the wall of the catheter.

This can be accomplished in any suitable fashion, but likely will be easiest to form if the formable length (or even the entire length of the catheter if the formable length is less than the entire length of the catheter) is formed of two separate tubular layers bonded to one another with the links between them. Such construction techniques are well known in the art and are used in creating catheters reinforced with tubular braid, as noted above.

Care should be taken to provide a wire lumen through the wall of the catheter between the spaced-apart links 240 so the control wires can be moved longitudinally. This can be accomplished using spacers to define the lumens, as noted above in connection with the wire lumens in the proximal length 20 (lumens 24 in FIG. 3). The gaps between adjacent links can instead be left empty, letting the wire lumens 244 in the links 240 guide the control wires along the length of the catheter.

The spacing between adjacent links can be adjusted to permit varying degrees of flexibility. As a general rule, as the links 240 are moved farther apart from one another along the catheter, the catheter will become increasingly flexible and the radius of curvature through which the catheter can be curved will become smaller. However, if the links are spaced too far from one another, this can compromise the lumen 12 of the catheter.

The relatively rigid links increase the rigidity of the catheter walls, defining a fairly round, open lumen. In the areas between links, where only the more flexible catheter wall is present, the catheter wall is more likely to deform. As is known in the catheter art, if a catheter is bent through too acute an angle, it will begin to "ovalize," i.e. its circular cross section will become more oval in shape, thereby reducing the minimum dimension of the lumen and decreasing its cross sectional area. In more extreme cases, the catheter can even kink, essentially folding on itself and practically closing the lumen entirely. If the catheter is to be used to deliver only fluids, some ovalization may be acceptable, but kinking should be avoided. If, however, a device is to be passed through the catheter (as in the case of a vascular sheath, for example), even relatively minor ovalization may preclude smooth passage of the device through the catheter.

The distance between the links 240 in a catheter such as that shown in FIGS. 8 and 9 should be chosen to maximize flexibility while ensuring a sufficiently patent lumen for the catheter to function effectively. The maximum desirable distance between links will depend on a number of factors, including the applications in which the catheter is to be used, the relative rigidities of the wall segments including a link and the wall segments without the links, and the absolute rigidity of the wall segments without the links. In appropriate circumstances, the anticipated anatomical constraints on the catheter when it is deployed in a patient can also allow a greater spacing because the patient's own tissues will help constrain the catheter from bending so acutely that it will excessively ovalize or kink.

While a preferred embodiment of the present invention has been described, it should be understood that various changes, adaptions and modifications may be made therein without departing from the spirit of the invention and the scope of the appended claims.

What is claimed is:

1. A remotely steerable catheter comprising:

a) an elongate tubular member having a proximal end, a distal end, a remotely manipulable length, and a flexible plastic wall defining a lumen; and b) first and second wires slidably retained by the wall and extending proximally beyond the proximal end of the tubular member, the first wire having a distal end thereof in controllable contact with the wall at a first node located along the manipulable length and the second wire having a distal end thereof in controllable contact with the wall at a second node located along the manipulable length, the second node being located distally of the first node along the manipulable length of the tubular member.

2. The catheter of claim 1 wherein the first and second control wires are attached adjacent the distal ends thereof to said first and second nodes, respectively.

3. The catheter of claim 1 wherein each of the first and second wires are slidably received within the wall of the tubular member.

4. The catheter of claim 3 further comprising first and second elongate channels extending within the wall, the first wire being slidably received within the first channel and the second wire being received within the second channel.

5. The catheter of claim 1 wherein each of the first and second nodes comprises at least one link formed of a material which is stiffer than said flexible plastic material of the wall.

6. The catheter of claim 1 wherein the remotely manipulable length of the catheter comprises the distal-most length of the catheter.

7. The catheter of claim 1 wherein the remotely manipulable length of the catheter comprises a plurality of relatively rigid links.

8. The catheter of claim 7 wherein each of the links is pivotably attached to at least one adjacent link, with each link having a lumen, the lumen of one link being in fluid communication with the lumen of each adjacent link.

9. The catheter of claim 7 wherein each link is encased in a flexible plastic material.

10. The catheter of claim 9 wherein the wall of the elongate tubular member is formed of said flexible plastic material, each link being imbedded in the wall.

11. The catheter of claim 7 wherein each link comprises a length of a relatively rigid tubular material, the links being spaced from one another along the remotely manipulable length of the catheter.

12. The catheter of claim 11 wherein the remotely manipulable length of the catheter further comprises a plastic material extending between each of said links, the plastic material being more flexible than the links.

13. The catheter of claim 1 wherein each of the first and second nodes comprises a distal link and a proximal link, the proximal and distal segments being moveable between an unlocked position wherein the links are free to pivot with respect to one another and a locked position wherein the links are constrained against relative movement.

14. The catheter of claim 13 wherein the distal and proximal links of each of the nodes are biased toward the unlocked position.

15. The catheter of claim 1 wherein the first and second wires are angularly spaced from one another around the wall.

16. The catheter of claim 15 wherein each of the first and second wires are slidably received within elongate channels within the wall of the tubular member, the elongate channels extending along the tubular member parallel to the tubular member's axis.

17. The catheter of claim 16 wherein the elongate channels are parallel to one another and spaced at least about 45 degrees from one another along the circumference of the wall.

18. The catheter of claim 15 wherein each of the first and second wires are slidably received within elongate channels within the wall of the tubular member, at least one of the elongate channels defining a helically oriented path along at least a distal portion of its length.

19. The catheter of claim 1 wherein the catheter extends proximally of the proximal end of the elongate tubular member.

20. A selectively formable catheter comprising:

a) an elongate tubular member having a proximal end, a distal end, a selectively formable length and a wall defining a lumen; and b) a distal locking segment and a proximal locking segment carried by the wall of the elongate tubular member and located along the selectively formable length thereof, the proximal and distal segments being selectively moveable between an unlocked position wherein the locking segments are free to pivot with respect to one another and a locked position wherein the locking segments are constrained against relative movement.

21. The catheter of claim 20 further comprising at least one control wire retained by the wall of the elongate tubular member, the control wire extending proximally from the distal locking segment to a location proximal of the proximal locking segment.

22. The catheter of claim 21 wherein the control wire extends proximally beyond the proximal end of the elongate tubular member.

23. The catheter of claim 20 wherein the distal and proximal locking segments may be releasably locked to one another, permitting them to be selectively returned to the unlocked position after reaching the locked position.

24. The catheter of claim 23 wherein the locking segments are biased toward their unlocked position.

25. The catheter of claim 24 further comprising a spring positioned between adjacent surfaces of the distal and proximal locking segments, the spring serving to so bias the locking segments.

* * * * *